United States Patent [19]

Inbar et al.

[11] Patent Number: 5,067,493

[45] Date of Patent: Nov. 26, 1991

[54] LITHOTRIPSY SYSTEM USING ULTRASOUND TO LOCATE CALCULI

[75] Inventors: Dan Inbar, Haifa; Daniel I. Barnea, Tel Aviv; Abraham Bruck, Haifa, all of Israel

[73] Assignee: Elscint Ltd., Haifa, Israel

[21] Appl. No.: 551,656

[22] Filed: Jul. 11, 1990

Related U.S. Application Data

[60] Continuation of Ser. No. 293,768, Jan. 5, 1989, abandoned, which is a continuation-in-part of Ser. No. 79,927, Jul. 31, 1987, abandoned, which is a division of Ser. No. 737,532, May 24, 1985, abandoned.

[51] Int. Cl.⁵ .............................................. A61B 17/22
[52] U.S. Cl. ............................. 128/660.03; 128/24 EL
[58] Field of Search ........................ 128/660.03, 24 EL

[56] References Cited

U.S. PATENT DOCUMENTS

| | | |
|---|---|---|
| 3,237,623 | 3/1966 | Gordon . |
| 3,735,755 | 5/1973 | Eggleton et al. . |
| 4,315,514 | 2/1982 | Drewes et al. . |
| 4,471,785 | 9/1984 | Wilson et al. . |
| 4,485,819 | 12/1984 | Igl . |
| 4,526,168 | 7/1985 | Hassler . |
| 4,539,989 | 9/1985 | Forssmann et al. . |
| 4,610,249 | 9/1986 | Makofski et al. . |
| 4,669,483 | 6/1987 | Hepp et al. ......................... 128/660.03 |
| 4,763,652 | 8/1988 | Brisson et al. ......................... 128/328 |
| 4,771,787 | 9/1988 | Wurster et al. ....................... 128/328 X |

FOREIGN PATENT DOCUMENTS

| | | |
|---|---|---|
| 2722252 | 11/1978 | Fed. Rep. of Germany ... 128/24 EL |
| 3127146 | 1/1983 | Fed. Rep. of Germany . |
| 3320998 | 12/1984 | Fed. Rep. of Germany . |
| 3703333 | 8/1988 | Fed. Rep. of Germany ...... 128/328 |
| 0278304 | 8/1988 | German Democratic Rep. .................................. 128/328 |

OTHER PUBLICATIONS

Pan et al., "Tomographic Reconstruction of Ultrasonic Attenuation with Correction for Refractive Errors", IBM J. Res Develop, vol. 25, No. 1, pp. 71–82, Jan. 1981.

Chaussey et al. ..., "Extracorporeal Shock Wave Lithotripsy", 1982.

*Primary Examiner*—Ruth S. Smith
*Attorney, Agent, or Firm*—Sandler, Greenblum & Bernstein

[57] ABSTRACT

A calculi locator is provided having at least one ultrasound transducers in combination with a shock wave generator. The ultrasound transducer is rotatable about the longitudinal axis of a reflector of the shock wave generator. The shock wave generator includes a target focal point. The transducer is used to assure positional coincidence of the true location of the calculi and of the target focal point. Alternatively, either a mathematical correction unit is used or iterative measurements are used to correct for refraction errors in the location of the imaged calculi.

5 Claims, 3 Drawing Sheets

FIG. 3A.
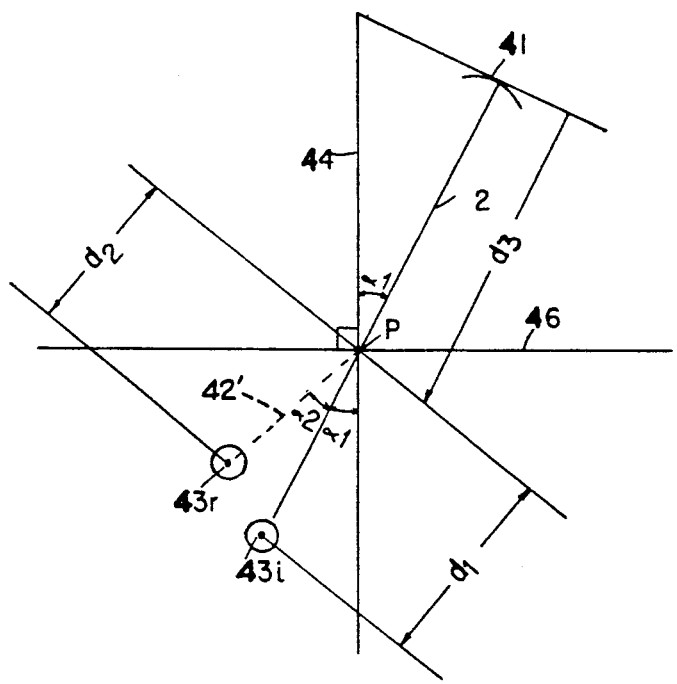
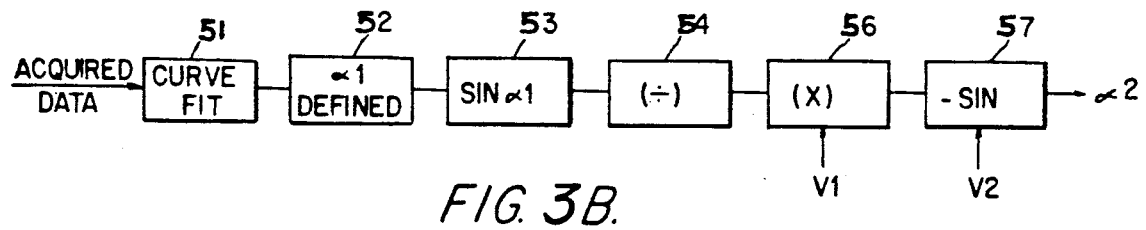
FIG. 3B.

_

LITHOTRIPSY SYSTEM USING ULTRASOUND TO LOCATE CALCULI

FIELD OF THE INVENTION

This application is a continuation of application Ser. No. 293,768, filed Jan. 5, 1989, now abandoned, which is a continuation-in-part of Ser. No. 079,927, filed July 31, 1987, now abandoned, which is a division of Ser. No. 737,532, filed May 24, 1985, now abandoned.

The invention of this Application is concerned with lithotripsy equipment for extra-corporeal fragmentation of renal calculi, and more particularly with imaging systems used for locating calculi in cooperation with lithotripsy type shock wave generators.

BACKGROUND OF THE INVENTION

One of the many ailments of mankind is the formation of calculi, that is stones or concrements, within the body. More common places for the development of such concrements are in the renal system and the gallbladder. Some of these stones pass through the renal system without causing any adverse affects noticed by the person having the stones. Other stones lodge within the kidney, the bladders or passageways between kidney, the bladder and the exterior of the body causing pain or impairing the operation of organs; then the removal of the calculi becomes imperative.

Originally the only way of removing these stones was through invasive surgery. With the advent of improved imaging techniques it became possible to utilize percutaneous techniques for the removal of many of the calculi. The percutaneous techniques are also invasive and require the insertion of means such as a nephrotomy catheter to accomplish the stone removal. The catheters are equipped with devices to grasp the calculi or ultrasonic generators for fragmenting the calculi by vibrating while contigious thereto.

More recently, extra corporeal shock wave lithotripsy has been applied to fragment and thereby eliminate renal calculi.

A lithotripsy system now being used has a pair of substantially orthogonally positioned X-ray generators designed to exactly locate the stone to be eliminated. The patient is moved three-dimensionally in a bath until cross-hairs on each of two images displayed by the system are juxtaposed to the stone. The cross-hairs are each at a line projection of the focal point of the shock wave generator. The patient is manipulated until the cross-hairs in each of the images are superimposed on the image of the stone; at that time the shock wave generator is triggered and the shock waves focused to shatter the stone down to sizes where the fragments will be washed out of the body through normal body functions.

The imaging systems used presently for the calculi locating function leave room for improvement. Among other things it is desirable to reduce the exposure of the patient to X-rays. The patient presently is exposed to X-rays, originally to ascertain that stones are indeed causing problems and that they can be eliminated by lithotripsy.

X-rays are used to align the stone with the focal point of the shock wave generator and X-rays are used subsequent to the application of the shock waves to assure that the stones have been shattered into fragments which can be disposed of by normal functions of the body. Thus, the procedure requires a relatively large accumulated dose of X-rays. It would be advantageous to lower the amount of X-ray radiation required in the lithotripsy process. To this end ultrasound has been tried in the past. Additionally ultrasound radiation is more capable of imaging gallbladder stones than X-ray radiation. However, the prior art attempts at imaging with ultrasound for locating calculi to be fragmented by shock waves have encountered difficulties.

In the prior attempts at using ultrasound as the medium for locating the calculi, different acoustic windows were used by the ultrasound transducers and by the shock wave generator. The prior systems also failed to make any effective correction for the distortions of the ultrasound signals and the shock waves due to refraction caused by the differences of the transmission velocities of the ultrasound signals and the shock waves in the different media.

In addition in the past no provisions were made for enabling a single ultrasound transducer to image a plurality of planes for assuring accurate location of the calculi.

Similarly, no provisions were made for varying the field of view of the individual transducers to provide for the different views required when searching for calculi and when centering the discovered calculi at the crosshairs.

Accordingly it is an object of the present invention to overcome the shortcomings of the prior art ultrasound imaging systems used in calculi location and to thereby improve on the presently available calculi locating imaging systems used in cooperation with extra corporeal shock wave lithotripsy.

BRIEF DESCRIPTION OF THE INVENTION

Accordingly a lithotripsy system including a calculi locator is provided for use in cooperation with shock wave generators having spark terminals at a source focal point of a reflector with a target focal point spaced apart therefrom, said lithotripsy system comprising:
  shock wave generator means for generating shock waves at a first focal point,
  a target focal point,
  means for causing said shock waves to focus on said target focal point,
  means for imaging the calculi within patients, said imaging means comprising:
  ultrasound scanning means for viewing said calculi to control the positioning of the calculi at the target focal point,
  means for moving said patient to enable positioning the calculi at the target focal point, and
  means for overcoming positioning errors caused by velocity difference in the various media traversed by the ultrasound signals in viewing the calculi in relation to velocity differences in the various media traversed by the shock waves when travelling from the first focal point to the target focal point for fragmenting the calculi.

A feature of the invention includes using ultrasound signal transducer means for imaging and combining the ultrasound transducer means with the shock wave generator means so that the focal points of an ultrasound transducer means and the shock wave generator means coincide. The system includes means for acquiring views of different planes through the coinciding focal points with the transducer means.

An alternative or related feature of the invention comprises means for computing and correcting the positioning errors caused by the differences between signal velocity and shock wave velocity travelling through different media; such as water and tissue.

A related feature of the invention comprises means for rotating said ultrasound transducer about the axis of the shock wave generator to provide various views of the calculi, while maintaining the coincidence of the target focal point and the transducer image cross-hair. In one embodiment the locations of the calculi obtained with the transducer in different positions are averaged to correct for positioning errors caused by refraction.

Another feature of the invention is the ability to image gallstones without the necessity of using dyes or the like.

Still a further feature of the invention comprises utilization of a pair of ultrasound transducers to speed the calculi locating process. The pair of ultrasonic transducers are arranged so that the cross-hair in the images generated by data from each of the transducers is truly on the target focal point of the shock wave generator. The planes imaged by each of the transducers are preferably orthogonal or at least at angles with respect to each other. Locating with each of the transducers individually overcomes positioning errors without the necessity of rotating the single transducer about the shock wave generator.

BRIEF DESCRIPTION OF THE DRAWINGS

The above named and other features and objects of the present invention will be best understood when considered in the light of the following description of selected embodiments of the invention taken in conjunction with the following drawings; wherein:

FIG. 3A is a line drawing to show positional errors caused by ultrasound signal and shock wave velocity differences in the different media traversed by the signals, and FIG. 3B is a block diagram showing positional error correction calculation means for use with the ultrasonic calculi locator.

GENERAL DESCRIPTION

Figure 1:
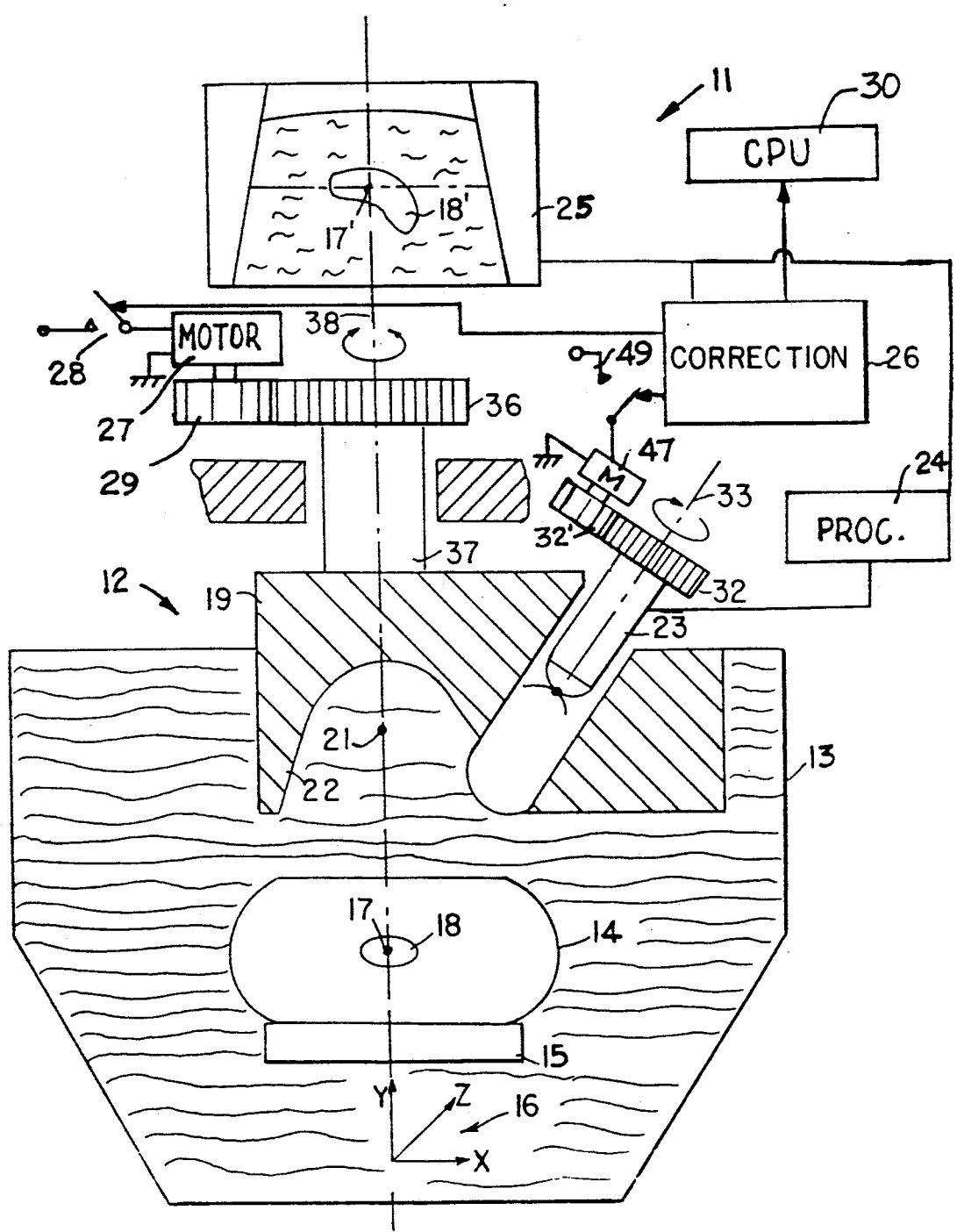
FIG. 1 is a sectional drawing of a lithotripsy system having an ultrasound calculi locator, showing an ultrasonic transducer removed from the shock wave generator window and capable of being positioned in a plurality of locations.

In the illustration of FIG. 1 a lithotripsy system 11 is indicated in combined cross sectional and block diagram form. The illustrated system comprises shock wave generator 12 which includes a bath 13 in which the patient 14 is partially submerged during the treatment. A hydraulic or mechanical system for supporting and moving the patient in the X, Y and Z directions is indicated by a bed 15. The axes of movement XYZ are shown generally at 16. The patient 14 is shown with a stone 17 located in a body organ such as a bladder, kidney or gallbladder indicated generally at 18.

The shock wave generator 12 has a pair of spark terminals, for example, indicated at 21. The location of the spark terminals is at a source focal point in a partial ellipsoid 22. The target focal point of the shock waves generated at the source focal point and reflected by the walls of the ellipsoid is at the location of the stone 17. The patient 13 is moved by movement of the bed 15 until the stone 17 is at the target focal point location.

It should be understood that while spark terminals are shown in the partial ellipsoid, the principal idea is that shock waves are generated by any means and focused by any suitable reflector at a target focal point so that the stone 17 may be set at the target focal point.

Means are provided for imaging the calculi, more particularly ultrasound transducer 23 is shown. The transducer in one embodiment is a sector scanning type of focused transducer. The bed 15 is moved until the calculi is at the transducer focal point with the transducer focal point coincident with the target focal point of the shock wave generator 12 at some time during its scan of an arc. The echoes received from the stone and from the body in general are processed in the normal manner of processing ultrasonic echo signals in image processor 24 to provide an image shown on the display means 25. The image includes an image of the calculi 17 located in the organ 18 of the patient 14.

Means are provided for overcoming the calculi location errors normally incurred with ultrasound waves due to refraction; i.e., in general to differences in the velocity of the ultrasound signals and the shock waves when travelling through the different media on the way to the calculi. The unique means include computer means indicated at block 26.

In the embodiment of FIG. 1 the transducer 23 is shown removed from being at the "window" location of the shock waves generated by the spark terminals 21. The computer means 26 provides a numerical or computational correction to overcome the calculi location errors. The correction afforded by unit 26 will be explained in greater detail hereinafter.

An additional feature and another way of aiding in overcoming the calculi location errors as shown in FIG. 1 is the capability to rotate the transducer 23 about the axis 38 of the shock wave generator 12. More particularly means are provided for rotating the transducer about the longitudinal axis of the ellipsoidal reflector of the shock wave generator 12. These means are indicated as the gear 36 shown at the top of column 37 fixedly attached to the shock wave generator 12. A motor 27 controlled through switch means 28 and coupled to gear 36 through gear 29 rotates shock wave generator 12 about the axis 38 responsive to and under control of the central processing and control unit (CPU) 30 of the lithotripsy system 11.

The rotation of the shock wave generator 12 causes the transducer 23 to rotate about the axis of rotation 38. The bed 15 is moved, if necessary, when the transducer stops at different positions to maintain the calculi at the transducer's focal point which is coincident with the focal point of the shock wave generator, i.e. to maintain the cross-hairs on the calculi. After movement of the bed the transducer is returned to the prior stone locating position to check that the cross hair is still maintained at the calculi. Alternatively, the amount of movement of the bed at different positions of the transducer 23 which is the measured differences in the position of the imaged calculi are averaged to overcome or reduce calculi location errors and the patient is moved to the calculated corrected position.

A system for assuring the rotational fidelity of the transducer is provided. More particularly, motor 47 is provided coupled to gear 32 through drive gear 32'. The motor is actuated responsive to the operation of switch 49 to cause the transducer 23 to rotate about its own axis 33 for assuring that the transducer is rotatively aligned with the focal spot. The switch 49 operates responsive to a signal from CPU 30 through correction unit 26. If the alignment of the transducer is true, the cross hairs remain on calculi 17 during the entire rotation.

Figure 2:
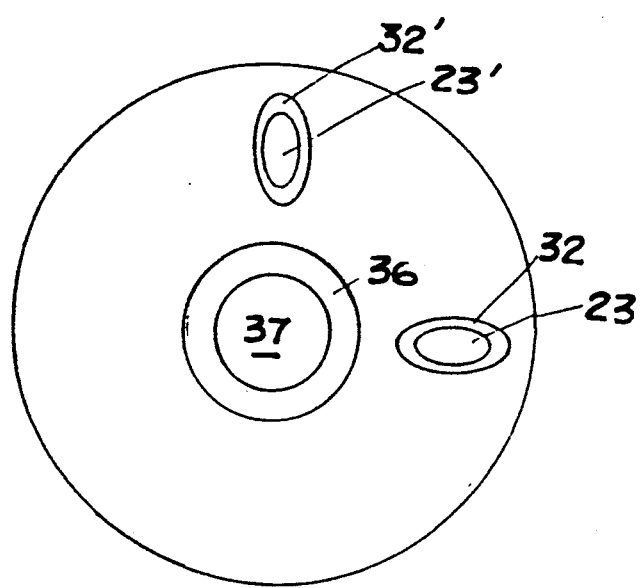
FIG. 2 is plan view of another embodiment of the ultrasound calculi locator which uses a plurality of transducers removed from the shock wave generator window and wherein the multiple transducers each remain in one location for calculi locating purposes.

FIG. 2 is a plan view of the spark generator 12. In the embodiment of FIG. 2 two transducers 23 and 23' are shown integrally located within the shock wave generator. In this arrangement there is no need to rotate the transducers about the axis of the spark gap shock wave generator. However, the transducers may be equipped to be rotated about their own axes, as indicated by gears 32 and 32'. The bed 15 is moved until the cross hairs in the image generated from data from each of the transducers are directly on target. This assures that the target is correctly located and errors due to refraction of the sound waves are minimized. When two transducers are used either two displays, one multiplexed display or one composite display, are shown on monitor 25.

FIG. 3 helps to explain the correction computations used to overcome the calculi location errors occurring because of the differences in the velocity of the shock waves and of the ultrasonic signals in the different media traversed in travelling to the calculi in the patient.

The ultrasound transducer 41 projects a series of beams as it scans over an arc. In FIG. 3A the arc of the series of beams is represented by the central beam 42. The beams cause echoes to be generated by tissue boundaries. The calculi generates such an echo.

The system normally treats the beam and the echo as if they had travelled along a straight line. Actually because of the differences between the velocity of the sound waves in water and in tissue, the calculi 43 which really is at location 43r appears at location 43i. Thus, there is an angular error $\alpha 2 - \alpha 1$ and a distance error $d1 - d2$, where:

$\alpha_1$, is the angle between the beam 42 and the normal 44 to the skin surface 46 at point p, where the beam is incident to the skin surface, $\alpha_2$, is the angle between the refracted beam 42' and the normal to the skin surface at the point p, d1 is the distance from point p to the apparent position of 43i of the calculi, and d2 is the distance from the point p to the actual position 43r of the calculi.

The angles and the velocities are related by Snell's Law:

$$\frac{\sin\alpha 1}{\sin\alpha 2} = \frac{V1}{V2}$$

where:

V1 is the velocity of sound in water, (1500 m/sec) and
V2 is the average velocity of sound in tissue, (1540 m/sec).

The distance d2 is easily determined. The time t1 for the echo to return from the calculi is known. That time multiplied by the velocity of sound in the tissue gives the distance to the calculi along beam 42'.

Normally the distance between the source and the object using a single velocity results in an error along the direction of the vector as well as an angular deviation due to Snell's law. During the first few frames of the scan the ultrasonic system will detect the position 46 of the skin surface. The position of the skin surface stands out because, as is well known, it is the first strong echo received.

FIG. 3B shows an embodiment of equipment for calculating the angle between the ultrasound beam and the normal to the skin surface for every imaging vector. A curve is fit to the data obtained to indicate the skin surface 46. Thus FIG. 3B shows a curve fitting means 51. The curve fitting means could be any well known means for curve fitting, such as a mean square operator using the data obtained at the skin.

After a curve is fitted, the angle $\alpha 1$ between the normal to the skin and the beams going from the transducer to the patient is obtained in means 52. The angle is obtained for each of the beams incident to the skin.

The sin of the angle $\alpha 1$ is calculated at 53 and divided by the velocity value V1 at block 54. The quotient is multiplied by the velocity V2 at multiplier 96 which gives a value of sin $\alpha 2$. The angle $\alpha 2$ is obtained from this value at operator 57. The value of $\alpha 2$ enables finding the actual line (i.e. line 42') for each of the beams upon which the real calculi is located.

Similar calculations may be made for correcting the shock wave generator target focal point for positional errors due to velocity differences and refraction. The corrected transducer focal point is set to coincide with the corrected target focal point.

In practice the lithotripsy equipment comprising the assembly of an ultrasonic transducer and a shock wave generator is used to determine the location of calculi and to destroy the calculi with shock waves generated extracorporeally. The actual location of the calculi is obtained either by: rotating one transducer about the axis of the shock wave generator and if necessary averaging calculi locations obtained or using two transducers without rotation about the shock wave generator axis.

The actual location of the calculi is shown on the image and the patient is moved until the cross hairs on the image coincide with the imaged calculi. At which time, the shock wave generator is triggered. After a series of shock waves have been generated and transmitted to fragment the calculi, the image is again provided to check to see if the calculi has indeed been fragmented and to further check and see if any of the fragments need further fragmentation.

While the invention has been described with regard to specific embodiments it should be understood that these embodiments are made by way of example only and not as a limitation on the scope of the invention, which is defined by the appended claims.

What is claimed is:

1. A lithotripsy system having:
    shock wave generator means for generating shock waves to destroy calculi,
    a calculi locator in combination with said shock wave generator means for obtaining an image of the calculi and for locating said calculi in a patient,
    said shock wave generator means comprising:
    an ellipsoidal reflector having a longitudinal axis,
    spark terminals located at a source focal point in said ellipsoidal reflector,
    a target focal point spaced apart from said spark terminals,
    said calculi locator comprising:
    ultrasound transducer scanning means for transmitting ultrasound waves and receiving echo waves, means for using said echo waves from said transducer means for acquiring an image of the location of said calculi in said patient, means for assuring coincidence of the true location of the calculi and the shock wave generator means target focal point, said means for assuring coincidence including:

means for mounting said transducer means on said ellipsoidal reflector spaced apart from said longitudinal axis of said ellipsoidal reflector for obtaining different views of the calculi at different locations of said transducer means around the longitudinal axis of said ellipsoidal reflector, and means for correcting for refraction of the waves by changing the patient position to maintain said calculi at the target focal point in said different views.

2. The lithotripsy system of claim 1 wherein said transducer means comprises a single transducer, said means for assuring coincidence including:

means for determining the average location of the imaged calculi by rotating the single transducer around the longitudinal axis between at least two different angular positions to obtain different views of the calculi imaged at the target focal point, said means for determining the average location of the imaged calculi including means for measuring changes in patient's position required to maintain the imaged calculi at the target focal point in said different views, means for averaging said measured changes, means for using the average measured changes as the change to obtain an average location, and said means for changing the patient's position to place said calculi at the target focal point in said different views comprising means for moving said patient's position to place said calculi at said average location.

3. The lithroptripsy system of claim 1 wherein said transducer means comprises a plurality of transducers, each of said plurality of transducers being angularly spaced from another of said plurality of transducers, said transducers being focused and each being positioned with the transducer focused on the target focal point of said shock wave generator means.

4. An ultrasound calculi locator operating in combination with shock wave generator means in a lithotripsy system including a water bath for destroying calculi in a patient immersed in said water bath, said shock wave generator means comprising:

an ellipsoidal mirror for focusing shock waves generated at a source focal point onto a target focal point to destroy calculi located at the target focal point, said ellipsoidal mirror having a longitudinal axis, said ultrasound calculi locator comprising:

an ultrasound transducer means for acquiring images of the calculi in the patient, said transducer means being mounted on said ellipsoidal mirror spaced apart from said longitudinal axis, means for rotating said ellipsoidal mirror about said longitudinal axis to revolve said transducer means around the longitudinal axis for at least a part of a revolution to obtain different views of the calculi, said transducer means being positioned to be focused on the target focal point of said ellipsoidal mirror throughout the at least a part of the revolution of the transducer means, correcting means for correcting for refraction when acquiring said images at each of said different views, said correcting means comprising:

means for determining the patient's skin surface image location, means for obtaining the angle $\alpha 1$ between a straight line from the transducer means to an image calculi at the target focal point and a line normal to the patient's skin surface where the straight line intersects the skin surface, means for obtaining the sin $\alpha 1$, means for dividing sin $\alpha 1$ by V1, the velocity of sound in water to obtain a quotient, means for multiplying the quotient by V2, the velocity of sound in tissue, to provide sin $\alpha 2$ where $\alpha 2$ is the angle of refraction, means for determing the angle of refraction from the arosin $\alpha 2$, means for correcting the image location of the calculi using the determined angle of refraction $\alpha 2$ to find the true location of the calculi, and means for moving the patient to move the true location of the calculi to the target focal point.

5. A calculi locator in combination with a shock wave generator for locating and destroying calculi in a patient undergoing lithotripsy, said shock wave generator comprising:

an ellipsoidal mirror for focusing shock waves generated at a source focal point onto a target focal point, said ellipsoidal mirror having a longitudinal axis, spark gap terminals at the source focal point for generating shock waves, said calculi locator comprising:

a single ultrasound transducer for transmitting ultrasonic beams and receiving echo signals, said ultrasound transducer attached to the ellipsoidal mirror at a position removed from the longitudinal axis, means for revolving the ultrasound transducer around said longitudinal axis for at least a part of a revolution to obtain different views of said calculi, said ultrasound transducer being in a position so that a central beam of said transmitted ultrasonic beam intercepts the target focal point throughout said at least part of said revolution, means for using said echo signals for acquiring images at the locations of said calculi in the patient, and means for moving said patient to move said calculi in the image to coincide with said target focal point.

* * * * *